(12) United States Patent
Biel et al.

(10) Patent No.: US 8,146,611 B2
(45) Date of Patent: Apr. 3, 2012

(54) METHOD AND APPARATUS FOR CLEANING OPHTHALMIC LENSES

(75) Inventors: Roger Biel, Aschaffenburg (DE);
Günter Lässig, Obernburg (DE)

(73) Assignee: Novartis AG, Basel (CH)

( * ) Notice: Subject to any disclaimer, the term of this patent is extended or adjusted under 35 U.S.C. 154(b) by 832 days.

(21) Appl. No.: 11/823,088

(22) Filed: Jun. 26, 2007

(65) Prior Publication Data

US 2008/0257387 A1 Oct. 23, 2008

(30) Foreign Application Priority Data

Jun. 26, 2006 (EP) .................................. 06013095

(51) Int. Cl.
*B08B 3/04* (2006.01)
(52) U.S. Cl. ..................... 134/104.3; 134/109; 134/133
(58) Field of Classification Search ........................ None
See application file for complete search history.

(56) References Cited

U.S. PATENT DOCUMENTS

| | | | | |
|---|---|---|---|---|
| 3,586,012 A | 6/1971 | Paule | | 134/93 |
| 4,852,592 A | 8/1989 | DiGangi et al. | | 134/57 |
| 4,971,765 A | 11/1990 | Loretti et al. | | 422/116 |
| 5,690,750 A | * | 11/1997 | Inada et al. | 134/11 |
| 2002/0150863 A1 | 10/2002 | Bennett | | 433/215 |
| 2002/0166578 A1* | 11/2002 | Leblond | | 134/99.2 |
| 2003/0178862 A1* | 9/2003 | Hagmann et al. | | 294/1.2 |

FOREIGN PATENT DOCUMENTS

| | | |
|---|---|---|
| EP | 1 262 306 | 12/2002 |
| EP | 1 449 543 | 8/2004 |
| WO | WO 98/19826 | 5/1998 |

OTHER PUBLICATIONS

PCT International Search Report.
PCT Written Opinion of the International Searching Authority.

* cited by examiner

*Primary Examiner* — Michael Kornakov
*Assistant Examiner* — Ryan Coleman
(74) *Attorney, Agent, or Firm* — Sheng-Hsin Hu

(57) ABSTRACT

The present invention relates to a method and a device for cleaning ophthalmic lenses, particularly contact lenses. The method and the device are suitable for integration into an automated production of ophthalmic lenses, particularly contact lenses.

4 Claims, 5 Drawing Sheets

METHOD AND APPARATUS FOR CLEANING OPHTHALMIC LENSES

This application claims benefit under 35 USC §119 of European patent application No. EP 06013095.2 filed Jun. 26, 2006, the contents of which are incorporated herein by reference.

The present invention relates to a method and a device for cleaning ophthalmic lenses, particularly contact lenses. The method and the device are suitable for integration into an automated production of ophthalmic lenses, particularly contact lenses.

A known method for producing ophthalmic lenses, particularly contact lenses, is the photochemical polymerization or crosslinking of suitable prepolymers in casting moulds. These casting moulds are either plastic casting moulds (preferably polypropylene (PP) or polyethylene (PE), but also polycarbonate (PC) and polyethylene terephthalate (PET)) for one-off use, or glass and/or quartz casting moulds for multiple use. Preferred polymers, resulting from the photochemical polymerization of suitable prepolymers, are polymers based on polyvinyl alcohols (PVA) or silicone hydrogels, but also those based on polyethylene glycols (PEG).

The ophthalmic lenses produced according to this method by photochemical polymerization are usually removed from the casting moulds and subjected to quality control before being forwarded for packaging or for further processing steps.

Before the quality control, and at the very latest before the ophthalmic lenses are packaged, they have to be cleaned, particularly in order to remove non-polymerized constituents of the prepolymer, but also in order to replace or remove any solvents that have been used in the method.

In production methods known from the prior art, the cleaning is done either still in the casting mould or, alternatively, on the gripper that conveys the ophthalmic lenses from the casting mould to the packaging or to further processing steps. The cleaning is usually carried out with the liquid used in the production method, preferably water. In many cases, the cleaning in the casting mould or on the gripper is incomplete, because the liquid used for the cleaning does not reach all the areas of the ophthalmic lens.

U.S. Pat. No. 3,586,012 discloses a manual contact lens cleaning device with a lens receiving basket in the fluid passageway to retain the lens while cleaned with a lens treating composition.

EP-A-1262306 discloses a system and method for treating ophthalmic lenses with fluids, wherein the lenses are retained in baskets in a vessel having two entrances/exits for fluids. The ophthalmic lenses are treated by continuously flushing with treating fluids in (multiple) reversed flows.

U.S. Pat. No. 4,852,592 discloses an apparatus for the cleaning of contact lenses comprising a two compartment lens encasing member in a cleaning chamber, being in fluid communication with a plurality of conduits for cleaning the lenses in fluid flow.

So far, no method or device for cleaning ophthalmic lenses suitable for integration into an automated production of ophthalmic lenses is known in the art.

It has now been found that a vessel with an inlet and an outlet for liquids, where at least part of the outlet is formed by first openings in the vessel wall and at least part of the outlet is formed by a second opening at the base of the vessel, which opening is designed such that an ophthalmic lens, particularly a contact lens, can enter and/or leave the vessel together with at least some of the liquid, is suitable for complete cleaning of ophthalmic lenses in an automated production of ophthalmic lenses. It has also been found that a preferred embodiment of the vessel according to the invention is suitable for replacing the liquid used in the method.

Figure 1:
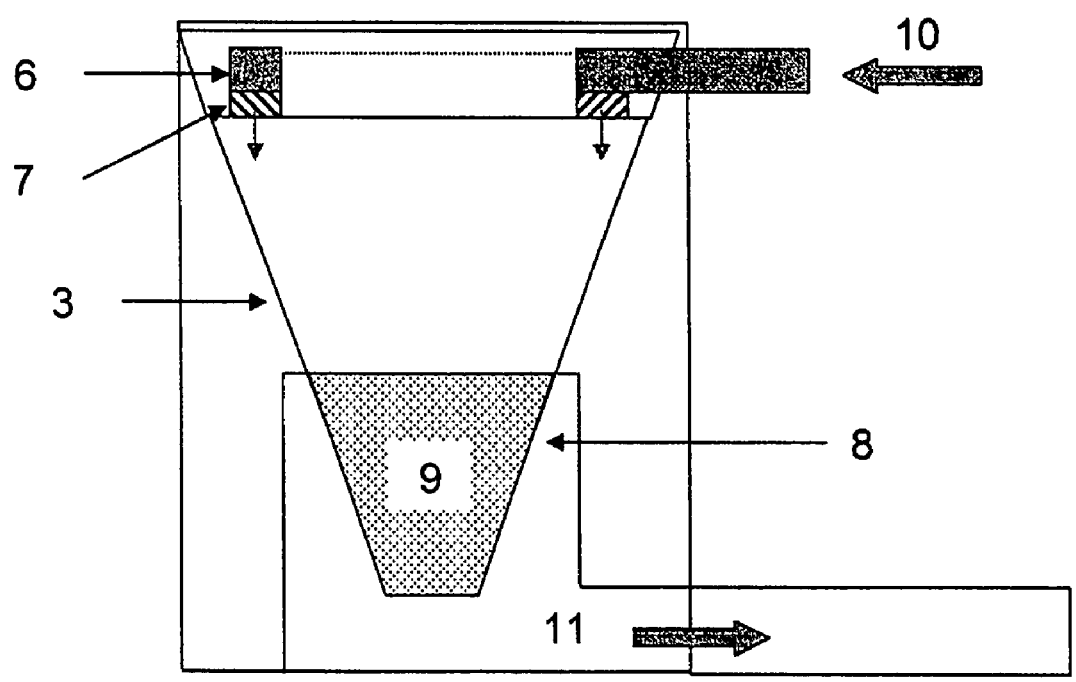
FIG. 1 shows a vessel for lens cleaning without a lens outlet (second opening) at the bottom.

A vessel 3 with a liquid chamber 9 without a lens outlet (second opening) at the bottom is shown in FIG. 1. Liquid is delivered through an admission line 10 into an annular conduit 6 and can then flow from admission openings 7 into the vessel 3. The liquid chamber 9 also comprises through-openings 8 through which liquid can flow into a discharge line 11. A lens can be delivered and removed from the vessel only from the top, e.g. by means of a gripper device (not shown here).

Figure 2:
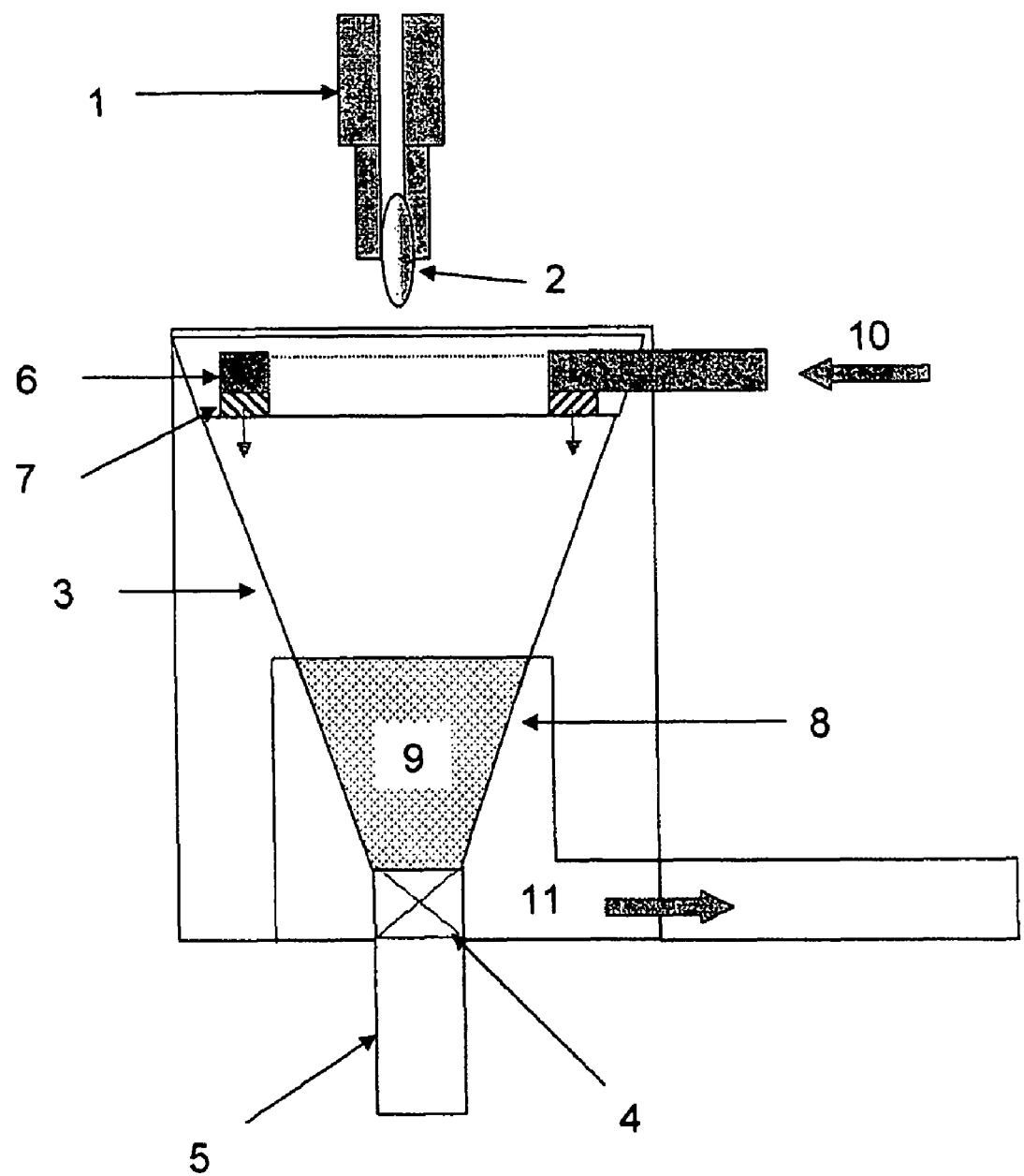
FIG. 2 shows the vessel from FIG. 1 with a closed lens outlet (second opening) at the base, and a gripper with lens.

A vessel 3 with a liquid chamber 9 is shown in a particularly preferred embodiment in FIG. 2. Liquid is delivered through an admission line 10 into an annular conduit 6 and can then flow from admission openings 7 (designed as nozzles in a particularly preferred embodiment) into the vessel 3. The liquid chamber 9 also comprises through-openings 8 (in a particularly preferred embodiment the vessel 3 is designed as a sieve in one area) through which liquid can flow into a discharge line 11. Moreover, a closed ball valve 4, shown at the base of the liquid chamber 9, seals off the liquid chamber at the bottom. A collection container 5 is arranged underneath the ball valve 4. A gripper 1 with a lens 2 is shown above the vessel 3, which lens 2 is delivered to the vessel in order to be cleaned.

Figure 3:
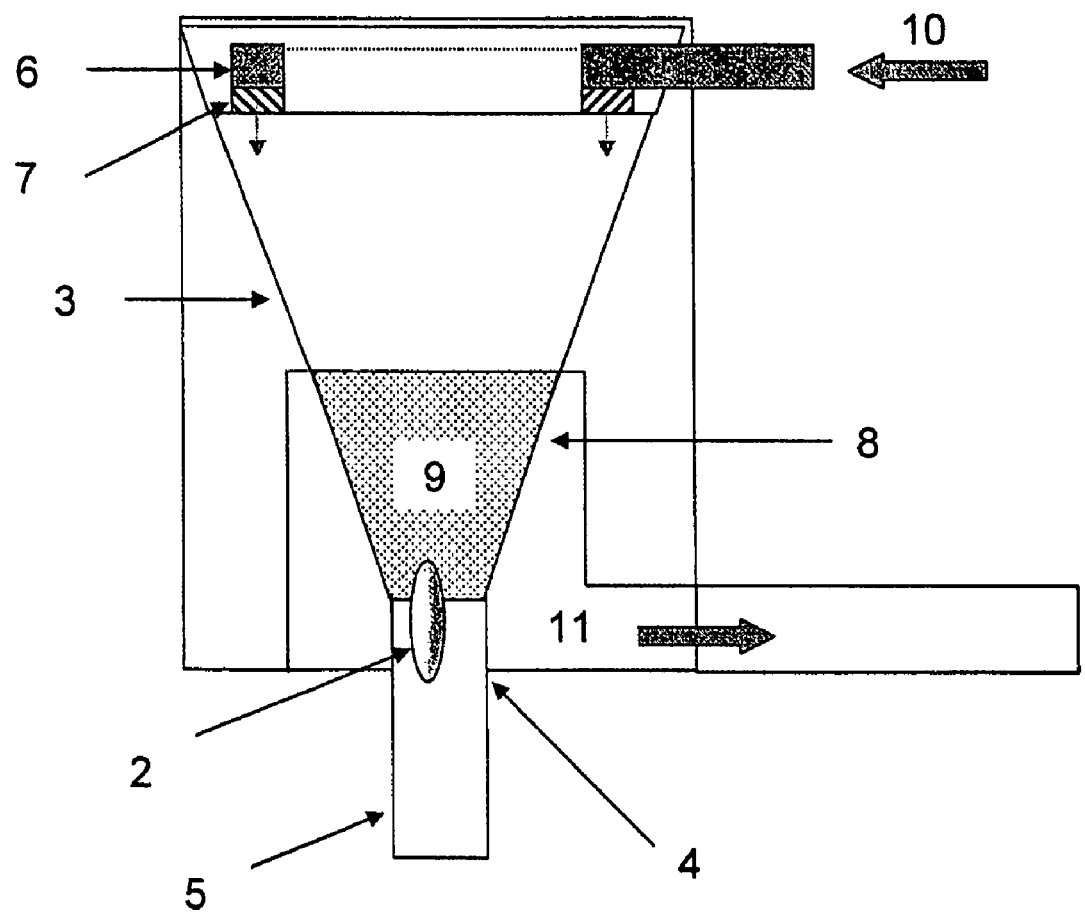
FIG. 3 shows the vessel from FIG. 2 when the lens outlet (second opening) at the base is open.

A vessel 3 with a liquid chamber 9 is shown in a particularly preferred embodiment in FIG. 3. Liquid is delivered through an admission line 10 into an annular conduit 6 and can then flow from admission openings 7 (designed as nozzles in a particularly preferred embodiment) into the vessel 3. The liquid chamber 9 also comprises through-openings 8 (in a particularly preferred embodiment the vessel 3 is designed as a sieve in one area) through which liquid can flow into a discharge line 11. Moreover, the base of the liquid chamber 9 is provided with an opened ball valve 4 through which the lens 2, together with some of the liquid, leaves the vessel after the cleaning operation and passes into the collection container 5 arranged underneath the ball valve.

Figures 4A, 4B, 4C:
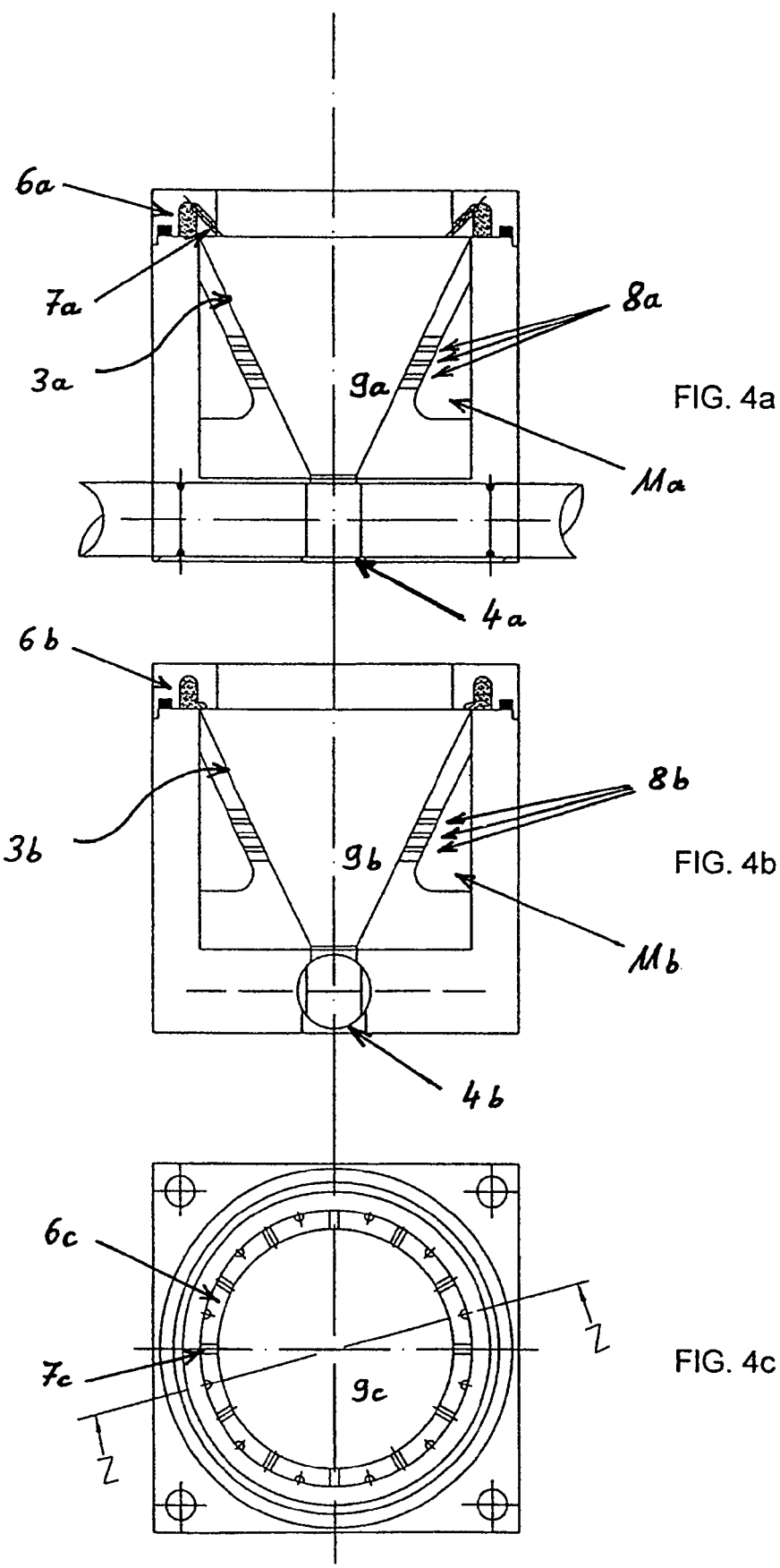
FIG. 4 (a-c) shows particularly preferred embodiments of a vessel with passages (first openings) in the vessel wall, with a lens outlet (second opening) at the base, and with nozzles arranged in a ring shape at the upper edge of the vessel.

FIG. 4a-c shows a particularly preferred embodiment of a vessel (3a; 3b) with a liquid chamber (9a; 9b; 9c). Liquid is delivered through an admission line (not shown here) into an annular conduit (6a; 6b; 6c) and can then flow through admission openings (7a; 7c) designed as nozzles into the vessel (3a; 3b). The liquid chamber (9a; 9b; 9c) also comprises through-openings (8a; 8b) through which liquid can flow into a discharge line (11a; 11b). The base of the liquid chamber (9a; 9b) is provided with a shaft with a bore (4a; 4b) which closes off or opens the liquid chamber from the bottom, to allow the lens (with some of the liquid) to leave the vessel after the cleaning operation.

Figure 5:
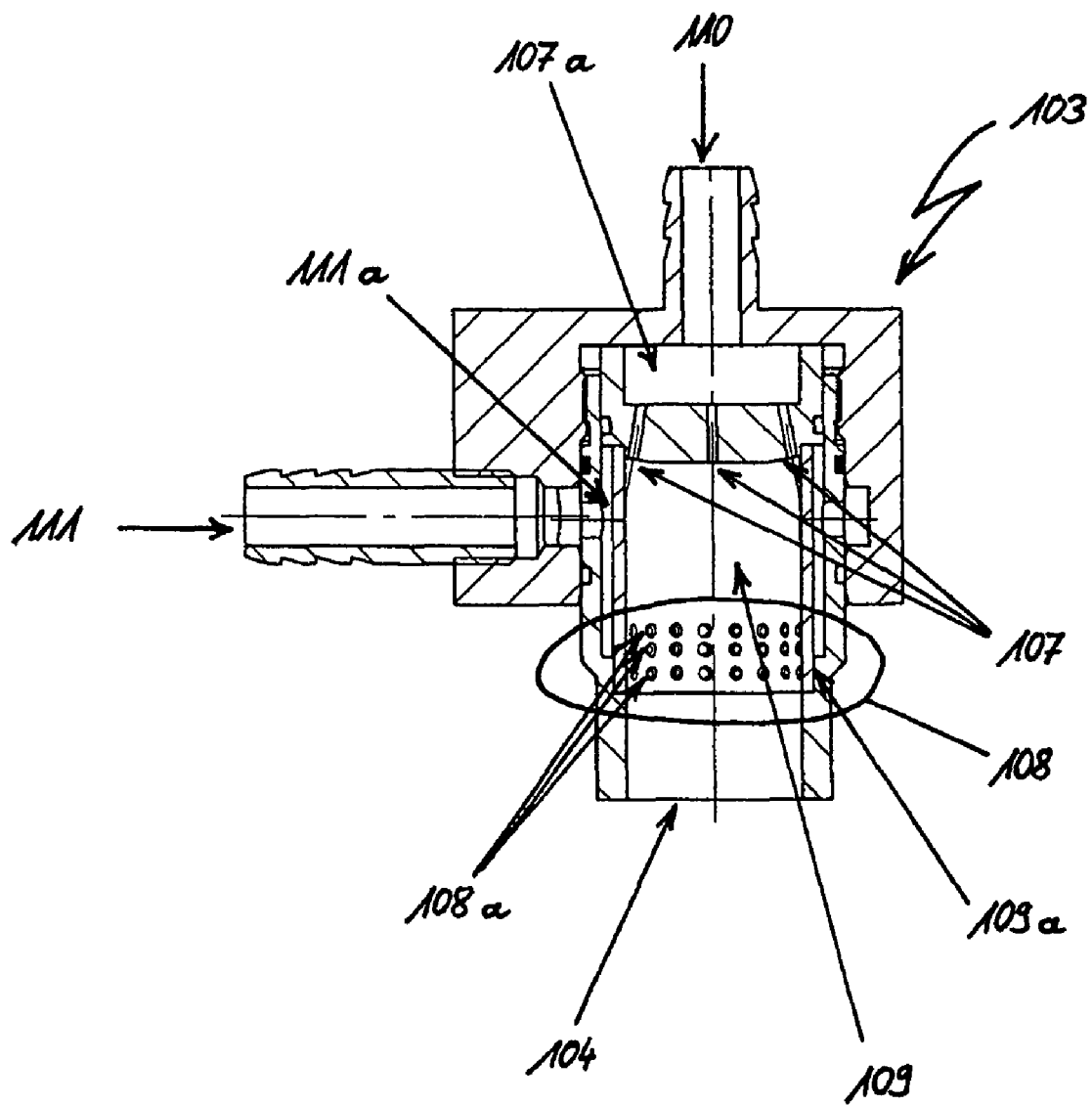
FIG. 5 shows a preferred embodiment of a lens cleaning unit according to the invention with a sieve outlet (first opening) and a lens outlet (second opening) at the bottom.

FIG. 5 shows another particularly preferred embodiment of a vessel (103) with a liquid chamber (109). Liquid is delivered through an admission line (110) via an admission chamber (107a) to admission openings (107) above the liquid chamber. The liquid chamber (109) comprises through-openings (108a) in the wall (109a) of the liquid chamber, designed as a sieve (108) in the lower portion of the liquid chamber. The vessel further comprises a discharge line (111) connected to (the outer side of) the sieve (108) via a discharge chamber (111a). The opening (104) at the bottom of the liquid chamber in a preferred embodiment may be (removably) closed by a suitable closure means, e.g. by a seal, plate, cap or by an opened ball valve (not shown here).

DESCRIPTION OF THE INVENTION

The device according to the invention and the method according to the invention for cleaning ophthalmic lenses are set forth in the claims.

The device according to the invention for cleaning ophthalmic lenses, particularly contact lenses, comprises a vessel which has an inlet and an outlet for liquids and into which ophthalmic lenses, particularly contact lenses, can be introduced for cleaning and can be removed again thereafter, at least part of the outlet being formed by first openings in the vessel wall, and at least part of the outlet being formed by a second opening at the base of the vessel, by means of which an ophthalmic lens, particularly a contact lens, can enter or leave the vessel together with at least some of the liquid (e.g. after the cleaning operation).

At least some of the outlet openings are arranged in the vessel walls. Further outlet openings can be arranged at the upper edge of the vessel (overflow) or at the base of the vessel (drain). In a preferred embodiment, the vessel is designed as a sieve at least in one area.

The inlet openings are arranged in the vessel walls, at the base of the vessel, or preferably at the upper edge of the vessel.

A vessel shape with the fewest possible dead spaces (or no dead spaces) is particularly preferred, especially a funnel-shaped vessel.

The through-openings (first openings) in the vessel wall (or the part of the vessel designed as a sieve) are designed such that not all the through-openings can be closed at the same time by a lens. This is achieved either by the number or the spatial arrangement of the through-openings.

The through-openings are chosen to be small, such that a lens cannot escape through these through-openings. The through-openings have a diameter of less than 2 mm, preferably less than 1 mm, and particularly preferably less than 0.5 mm. The smaller the through-openings are, the greater the number of such through-openings that have to be arranged in the vessel wall in order to ensure a sufficient flow of the liquid. At least part of the vessel wall is preferably designed as a sieve, particularly preferably up to 50% of the vessel wall. The part of the vessel wall designed as a sieve is preferably the lower part of the vessel.

In another preferred embodiment, the vessel is arranged in such a way that one or more lenses can be placed into the liquid chamber by means of a gripper. The vessel is also arranged in such a way that the one or more lenses can be removed from the vessel by means of a gripper. Suitable grippers are pincer-type grippers or vacuum grippers, for example grippers with a large or small suction surface. A suction surface is defined as large if it has a diameter of 20% or greater, preferably of 50% or greater, particularly preferably of 80% or greater, relative to the diameter of the lens that is to be gripped. However, other grippers in the form of a net or a sieve ladle are also conceivable.

The gripper for placement and removal is preferably a vacuum gripper, which is designed in such a way that the suction surface is small. A small suction surface with one or more holes is particularly preferred, and a small suction surface with one hole is very particularly preferred. A suction surface is defined as small if it has a diameter of 10% or less, preferably 5% or less, particularly preferably 1% or less, relative to the diameter of the lens that is to be gripped. A small suction surface ensures that only a single lens can be removed at a time from a vessel containing several lenses.

In another particularly preferred embodiment, the vessel is equipped with a spray device which allows the lens on the gripper to be flushed off into the vessel. The spray device can be designed in the form of one or more nozzles arranged at or over the edge of the vessel, particularly preferably as a ring of nozzles at the upper edge of the vessel. The spray device is suitable in particular for cleaning the lens on the gripper or particularly preferably for flushing the lens from the gripper into the vessel, e.g. in cases where placement of the gripper into the liquid in the vessel is made difficult by surface forces.

The second opening at the base of the vessel in one embodiment may be designed as an opening which can be closed, e.g. by placement of the entire vessel into a container, wherein the bottom of the container closes the second opening. In another embodiment the second opening may be designed as a ball valve which is closed during the cleaning operation and which is opened in order to allow the liquid to drain off with the lens. In another embodiment the second opening may be designed as a shutter device e.g. an iris diaphragm.

The second opening at the base of the vessel preferably has a diameter of 1 to 15 mm, preferably 4 to 10 mm, and particularly preferably 5 to 8 mm.

The device according to the invention is suitable for integration into an automated production device for ophthalmic lenses, particularly for contact lenses.

The invention further relates to a method for cleaning ophthalmic lenses, characterized by introducing one or more ophthalmic lenses into a vessel with an inlet and an outlet for liquids, where at least part of the outlet is formed by first openings in the vessel wall and that at least part of the outlet is formed by a second opening at the base of the vessel, which second opening is designed such that an ophthalmic lens, particularly a contact lens, can enter or leave the vessel together with at least some of the liquid,
cleaning the ophthalmic lens in the liquid in the vessel, and removing the cleaned ophthalmic lens from this vessel.

In a preferred method, one or more ophthalmic lenses are introduced by means of the ophthalmic lens being placed into the liquid by means of a gripper or by the ophthalmic lens being flushed off from the gripper by means of the liquid.

In a particularly preferred method, the removal of one or more cleaned ophthalmic lenses is effected by means of opening the second opening at the base of the vessel and allowing the contact lens to leave the vessel together with at least some of the liquid.

In another particularly preferred method, the cleaned ophthalmic lens is removed from the vessel by means of a gripper. The removal from the vessel takes place either from the liquid or from the vessel when partly or completely emptied of liquid, preferably from the liquid.

In a more preferred method, one or more ophthalmic lenses are introduced into the vessel through the second opening at the base of the vessel by a reverse flow of liquid into the vessel through the second opening, and the cleaned ophthalmic lens is removed from the vessel by means of opening the second opening at the base of the vessel and allowing the ophthalmic lens to leave the vessel together with at least some of the liquid.

A reverse flow in the meaning of the present invention is a mode of action where an outlet functions as an inlet and vice versa, e.g. upon closure of the discharge line, a suction force may be applied via the admission line, so that liquid may enter into the vessel through the second opening. In the same way upon closure of the admission line, a suction force may be applied via the discharge line, so that liquid may enter into the vessel through the second opening.

Finally, the invention also relates to a method for replacing liquids surrounding an ophthalmic lens, by introducing an ophthalmic lens, particularly a contact lens, into a vessel with an inlet and an outlet for liquids, where at least part of the outlet is formed by first openings in the vessel wall and that at least part of the outlet is formed by a second opening at the base of the vessel, which second opening is designed such that an ophthalmic lens, particularly a contact lens, can leave or enter the vessel together with at least some of the liquid, by placing the ophthalmic lens by means of a gripper into a first liquid or by flushing the ophthalmic lens off from the gripper by means of a first liquid, or by introducing the ophthalmic lens into the vessel through the second opening at the base of the vessel by a reverse flow of a first liquid into the vessel through the second opening,
replacing a first liquid with a second liquid by way of the inlet and outlet for liquids, and removing the ophthalmic lens from this vessel.

In a preferred method, the removal of one or more ophthalmic lenses is effected by opening the second opening at the base of the vessel and allowing the contact lens to leave the vessel together with at least some of the second liquid.

In another preferred method, the removal of the ophthalmic lens from the vessel is effected by means of a gripper. The removal from the vessel takes place either from the liquid or from the vessel when partly or completely emptied of liquid, preferably from the liquid.

In a particularly preferred method, the ophthalmic lens is cleaned in the respective liquid before or after the replacement of the liquids. The cleaning of the ophthalmic lens advantageously takes place in the first liquid before it is replaced by the second liquid.

The dwell time of the lens in the vessel for cleaning is from 1 to 10 seconds, preferably 2 to 8 seconds, particularly preferably 5 seconds. However, the dwell time can also be considerably longer, depending on the requirements of the method. For example, in the case of a solvent exchange (liquid exchange) or an extraction step in the vessel, the dwell time of the lens can be 60 seconds and more.

For a funnel-shaped vessel (with an approximately conical inner volume), the liquid volume is calculated according to $V_{cone} = \pi/3 \cdot r^2 \cdot h$, with radius r at the upper edge of the vessel (or at the liquid surface) and height h between the base and the upper edge of the vessel (or between the base and the liquid surface). This means that, for a vessel with a height of 5 cm and a diameter of 4 cm at the upper edge, the maximum liquid volume is approximately 20 ml. The filling level during the cleaning operation is between half the filling height and the full filling height, preferably ⅔ of the maximum filling height. In a vessel with the above-described dimensions, a liquid volume of 1 to 100 ml/s, preferably 5 to 80 ml/s, particularly preferably 10 to 50 ml/s is admitted and discharged during the cleaning operation.

A preferred method for cleaning ophthalmic lenses to be integrated into an automated production for ophthalmic lenses may be described as follows: A device (103) according to FIG. 5 is placed in a container comprising an ophthalmic lens in a liquid in such a way, that the lens can be introduced into the liquid chamber (109) through the second opening (104) by applying a suction force, e.g. either on the discharge line (111) with the admission line (110) being closed, or on the admission line (110) with the discharge line (111) being closed, or through a separate suction line (not shown in FIG. 5) in connection with the liquid chamber (109). Said suction force creates a liquid flow into the liquid chamber to introduce the lens into the liquid chamber (i.e. by a reverse flow). The liquid chamber may then be closed at the second opening (104) with a suitable closure, e.g. by pressing the second opening (104) onto the bottom of the container which is formed to receive the second opening and to close the second opening. To clean the lens (and/or to replace the first liquid with a second liquid) the admission line (110) and the discharge line (111) are opened and liquid is flushed through the admission chamber (107*a*) to the admission openings (107) into the liquid chamber (109) and through the sieve (108) via the discharge chamber (111*a*) to the discharge line (111). The time (in s) and the flow (in ml/s) determine the cleaning result and may be adapted to the lens cleaning requirements of the process (for preferred ranges see above). After the cleaning (and/or the replacement of the first liquid with a second liquid), the second opening (104) is opened again, e.g. by lifting the second opening (104) form the bottom of the container and the lens is released, with the remaining liquid in the liquid chamber, into the container.

A liquid replacement can be carried out as follows: In a first procedure, a change-over is made from a first liquid to a second liquid, with the flow through the admission line being kept constant. This initially results in a mixture of the first liquid and second liquid in the vessel. As this mixture is drained off, however, the proportion of the second liquid in the vessel increases continuously until the first liquid has been completely replaced by the second liquid.

In a second procedure, the delivery of the first liquid can initially be interrupted until the amount of liquid in the vessel has decreased as a result of the continuous draining to a small residual volume, which is still just enough to completely surround the lens. Only then is the delivery of the second liquid started. Although this also initially results in a mixture of the first liquid and second liquid in the vessel, the first liquid is nevertheless present in a much smaller proportion. As this mixture drains off, the proportion of the second liquid in the vessel increases continuously until the first liquid has been replaced completely by the second liquid.

In a third procedure, the delivery of the first liquid can be interrupted until the first liquid has drained completely from the vessel and the lens lies dry. Only then is the delivery of the second liquid started. This means that no mixture of the first liquid and second liquid arises (apart from first liquid that adheres to the lens or is bound within the lens). This procedure is suitable in particular for replacement of liquids with unfavourable mixing properties or very different surface forces.

Suitable liquids are water, water containing one or more disinfecting ingredients, salt solutions or buffered solutions, for example saline, and organic solvents, for example ethanol.

EXAMPLES

The cleaning action of the device according to the invention was investigated in a laboratory test with a funnel-shaped vessel (shown schematically in FIG. 2 and FIG. 3). The detailed technical configuration of the funnel-shaped vessel can be seen from FIG. 4*a*-*c*.

The nozzles (7a) arranged in a ring shape were made of stainless steel, the funnel-shaped vessel (3a; 3b) was made of polyacetal (POM) plastic in a housing of aluminium, and the drain (4a; 4b) at the base of the vessel was made of stainless steel and Teflon.

The funnel-shaped vessel had a height of 5 cm and a maximum diameter of 4 cm. Water was delivered through nozzles (diameter 0.8 mm) arranged in a ring shape at the upper edge of the vessel. The vessel was designed with through-openings which extended to ½ its height and through which water could be removed. The flow throughput in the laboratory test was between 0.9 and 1.1 l/min.

To produce contact lenses with defined contamination, they were smeared with polyvinyl alcohol (PVA) sol and with polyethylene glycol (PEG) sol. Lenses with 5 mg, 10 mg and 20 mg contamination were produced.

The uncontaminated lens, the contaminated lens and the cleaned lens were each weighed. Using a pincer-type gripper, a contaminated lens was placed into the funnel-shaped vessel in the water jet of the annular nozzle. The lens was cleaned for a few seconds in the swirling water. The contaminated water flowed off via the sieve cone. When the drain at the base was opened, the lens was flushed into a collection container.

The results of the laboratory test were as follows:

The placement of the lens by the pincer-type gripper (or the flushing of the lens from the pincer-type gripper) is fast and reliable.

The cleaning time is dependent on the degree of contamination. With cold water (15-25° C.), up to 5 mg of PVA sol can be removed within a cleaning time of 5 seconds, this result being reproducible. With hot water (40-50° C.), up to 10 mg of PVA sol can be removed within 5 seconds, this result being reproducible. In the laboratory test, PEG sol was much easier to remove than PVA sol. With hot water (40-50° C.), up to 20 mg of PEG sol could be removed within 5 seconds, this result being reproducible.

The cleaning action deteriorated with increasing drying time and exposure of the sol to the air.

Throughout the laboratory test, there was not a single instance of a lens remaining stuck on the through-openings or in the drain at the base of the vessel.

The invention claimed is:

1. A device for cleaning ophthalmic lenses comprising:
a vessel configured to store an ophthalmic lens when the lens is being cleaned with cleaning liquid;
a gripper configured to grip an ophthalmic lens such that the gripper can place an ophthalmic lens within the vessel;
wherein the vessel comprises an inlet for liquids;
wherein the vessel comprises a sieve through which liquid in the vessel can pass to enter a discharge line, wherein the sieve is sized to prevent the passage of a stored ophthalmic lens through the sieve; and
wherein the vessel comprises an outlet below the sieve, wherein an ophthalmic lens can be discharged through the outlet with at least some of the cleaning liquid into a shaft having a bore that can be selectively opened and closed.

2. A device according to claim 1, characterized in that the inlet is designed in the form of nozzles that are arranged at an upper edge of the vessel.

3. A device according to claim 1, characterized in that the vessel is arranged in such a way that one or more lenses can be delivered for cleaning into the vessel through the outlet below the sieve.

4. A device according to claim 2, characterized in that the vessel is arranged in such a way that one or more lenses can be delivered for cleaning into the vessel through the outlet below the sieve.

* * * * *